United States Patent [19]

Chapman

[11] Patent Number: 4,643,175
[45] Date of Patent: Feb. 17, 1987

[54] DEVICE FOR ASSISTING AND MAINTAINING PENILE ERECTION

[76] Inventor: Kenneth Chapman, P.O. Box 735, Bellaire, Tex. 77401

[21] Appl. No.: 775,726

[22] Filed: Sep. 13, 1985

[51] Int. Cl.⁴ .............................................. A61F 5/41
[52] U.S. Cl. ...................................................... 128/79
[58] Field of Search ...................... 128/79, 138 R, 386

[56] References Cited

U.S. PATENT DOCUMENTS

| 609,614 | 8/1898 | Doty | 128/79 |
|---|---|---|---|
| 1,511,572 | 10/1924 | Marshall | 128/79 |
| 2,024,983 | 12/1935 | Street | 128/79 |
| 3,633,572 | 1/1972 | Wiggins | 128/79 |
| 4,022,196 | 5/1977 | Clinton | 128/79 |
| 4,381,000 | 4/1983 | Duncan | 128/79 |
| 4,429,689 | 2/1984 | Yanong | 128/79 |
| 4,440,183 | 4/1984 | Miller | 128/79 |
| 4,488,541 | 12/1984 | Garcia | 128/79 |

FOREIGN PATENT DOCUMENTS 2137097  10/1984  United Kingdom .................. 128/79

Primary Examiner—Gene Mancene
Assistant Examiner—Cary E. Stone
Attorney, Agent, or Firm—Bill B. Berryhill

[57] ABSTRACT

A device for assisting in and maintaining erection of the human penis, comprising: a relatively rigid arc member and an elastic cord extending from each end of the arc member and joined to form a large loop.

8 Claims, 5 Drawing Figures

U.S. Patent  Feb. 17, 1987  4,643,175
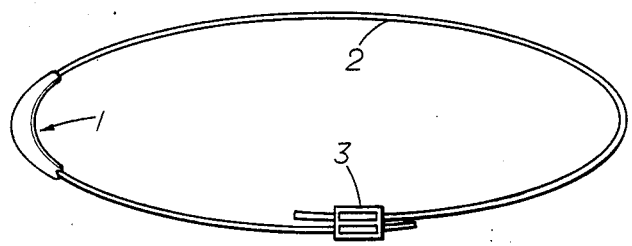
FIG. 1
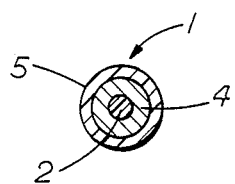
FIG. 2
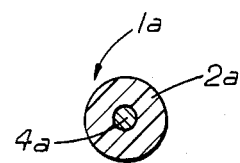
FIG. 3
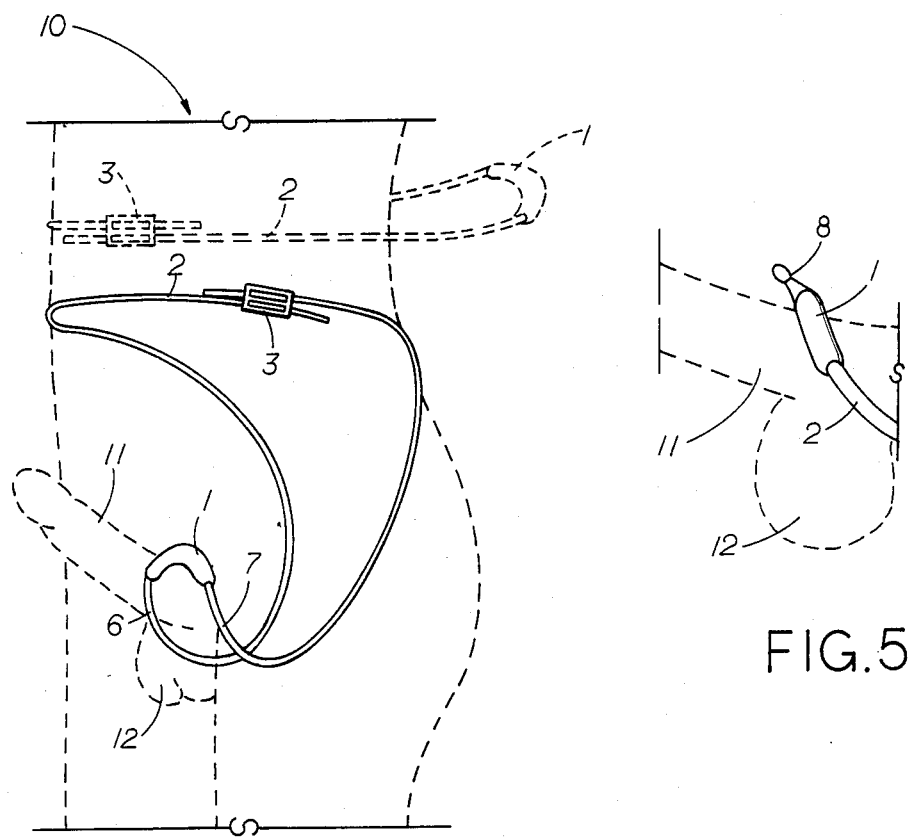
FIG. 4
FIG. 5

DEVICE FOR ASSISTING AND MAINTAINING PENILE ERECTION

BACKGROUND OF THE INVENTION

1. Field of the Invention

The present invention pertains to a device for assisting in and maintaining erection of the human penis.

2. Brief Description of the Prior Art

For various physical and mental reasons, some males are not able to attain and maintain penile erection, rendering satisfactory intercourse difficult or impossible. Even though most males may attain and maintain penile erections satisfactory for intercourse, the experience thereof could be enhanced for the male and his female partner so that the act of intercourse would be more satisfactory to both partners.

To aid those incapable of normal penile erection and to enhance the sexual experience of others, a number of devices have been invented to assist, maintain or substitute for penile erection. In some cases, surgical implanting of prosthetic devices have been utilized. Surgical procedures are avoided by most males. Such surgical procedures are usually expensive and are not without some degree of risk.

Other solutions to the problem of inadequate penile erection are provided by apparatus which may be worn and utilized by the male without surgical procedure. Some of these provide artificial support or rigidity by providing members to surround and/or support the penis and which are normally attached to the body with a harness-like arrangement. Examples may be seen in U.S. Pat. Nos. 4,022,196; 4,381,000; 4,429,689 and 4,488,541. These devices are rather cumbersome and relatively uneasy to use.

Other devices, proposed to assist in or maintain penile erection, function to exert pressure to or around the penis to control the return flow of blood therefrom, thus maintaining the penis in an erect condition. Some of these, such as U.S. Pat. Nos. 3,845,760; 3,461,863; and 3,612,047, function essentially as a tourniquet. Thus, there are some dangers involved if blood circulation is too severely restricted. In addition, the tourniquet-like device, while restricting blood flow, may also restrict and/or impede ejaculation, causing physical harm and/or pain.

Because of some of the problems inherent with tourniquet-like devices, other devices have been proposed which restrict blood flow from the penis but do not totally surround or clamp the penis so as to avoid the inherent problems thereof. Examples may be seen in U.S. Pat. Nos. 3,511,230; 3,633,572 and 4,440,183. While these devices are inherently safer, they are more difficult to maintain in proper position and the means for maintaining them in proper position is sometimes uncomfortable and detract from the user's sexual urge and enjoyment.

Obviously, with the continued development and proliferation of devices to aid in attaining and maintaining penile erection, the search continues for more effective and more comfortable solutions.

SUMMARY OF THE PRESENT INVENTION

The present invention provides a device for assisting in and maintaining penile erection. The device is relatively simple, comprising: a relatively rigid arc member and an elastic cord member extending from each end of the arc member and joined to form a large loop. The loop is positionable around the user's waist, with the arc member at the user's back, but permitting the arc member to be pulled between the user's legs for placement so as to engage the top of the penis at the base thereof. A clamp member may be provided for placement at opposite ends of the cord member so as to allow shortening and lengthening of the loop for placing more or less pressure at the penis base.

The resulting device is one which is extremely effective for assisting in and maintaining erection of the penis without the problems associated with other devices. It is extremely simple and easy to use so as not to detract from sexual urge. It is especially helpful to those who have difficulty in maintaining an erection. For those who have no difficulty in maintaining an erection, it simply may be used to provide a more satisfying sexual encounter. Many other objects and advantages of the invention will be understood by reading the description which follows in conjunction with the accompanying drawings.

BRIEF DESCRIPTION OF THE DRAWINGS

FIG. 1 is a perspective view of a preferred embodiment of the invention;

FIG. 2 is a cross-sectional view of a portion of the invention, according to a preferred embodiment thereof;

FIG. 3 is a cross-sectional view of a portion of the present invention, according to an alternate embodiment thereof;

FIG. 4 is a pictorial representation of the device of the present invention as it would be positioned for use;

FIG. 5 is an elevation view showing the device of the present invention, according to an alternate embodiment thereof, in position for use.

DESCRIPTION OF PREFERRED EMBODIMENTS

Referring first to FIG. 1, there is shown the device of the present invention for assisting in and maintaining erection of the human penis. The device comprises a relatively rigid arc member 1 and an elastic cord member 2 extending from each end of the arc member and joined to form a large loop. The ends of the cord 2 are shown joined by a clamp member 3.

The arc member 1, a cross-sectional of which is shown in FIG. 2, may include a relatively rigid tubular member 4 through the center of which the cord member 2 may pass. If desired, the tubular member 4 may be surrounded by a relatively soft cushioning material 5. The tubular member 4 is made of a relatively rigid material such as metal, but is preferably hand-deformable, allowing the arc member 1 to be slightly deformed as necessary.

An alternate embodiment of the arc member, designated 1a, is illustrated in cross-section in FIG. 3. In this embodiment, the elastic cord 2a is hollow and encases a short section of metal rod 4a or the like which is also hand deformable.

Referring now also to FIG. 4, the use of the device of the present invention will be described. With the device formed in the loop fashion of FIG. 1 so as to provide a loop of a few inches greater than the dimension of the waist of the user 10, the cord 2 is placed around the user's waist first with the arc member 1 at the user's back, illustrated by the dotted line position shown in FIG. 4. Then the user reaches with one hand, from the front, through his crotch, grasping the arc member 1 and pulling it between the legs, placing the arc member 1 in engagement with the top of the penis 11 at the base thereof. In this position (solid line), first and second portions 6 and 7 of the elastic cord member 2 extend from the arc member 1 on opposite sides of the user's scrotum 12 and back between the legs.

In the proper position of FIG. 4, the arc member 1 therefore applies pressure to the upper portion of the penis 11 near the base thereof, restricting blood flow therefrom. This thus assists in and maintains erection of penis 11. However, since the arc member 1 does not totally encircle the penis 11, blood flow is not totally interrupted and neither is ejaculation prevented or hindered. The blood restriction results in the penis being maintained at maximum rigidity until ejaculation. As previously mentioned, the clamp member 3, which can be made in a number of different ways, allows the loop formed by the elastic cord to be shortened and lengthened, thus placing more or less pressure, as desired, at the base of the penis 11. Since the portions 6 and 7 of the elastic cord 2 near the arc member 1 pass on opposite sides of the scrotum 12, there is no discomfort associated therewith.

In FIG. 5, an alternate embodiment of the invention is shown which provides greater satisfaction to the female partner of the user. In this embodiment, a protuberance 8 projects outwardly from the arc member 1 so as to provide clitoral stimulation to the user's partner during intercourse. The protuberance 8 can be made in any variety of shapes and would preferably be of a deformable material, such as rubber or plastic.

Thus, the present invention provides a device for assisting in and maintaining erection of the human penis. It does so in a very efficient and safe manner. It is simply constructed and easily used. While several embodiments of the invention have been described herein, many variations can be made without departing from the spirit of the invention. Accordingly, it is intended that the scope of the invention be limited only by the claims which follow.

I claim:

1. A device for assisting in and maintaining erection of the human penis, comprising:
   a relatively rigid arc member for engagement with the top of the penis at the base thereof; and
   an elastic cord member extending from each end of said arc member and joined to form a large loop, said loop being positionable around the user's waist with said arc member at the user's back and permitting said arc member to be pulled between the user's legs for placement in said engagement with said top of said penis at the base thereof, first and second portions of said cord member then extending from said arc member between the legs on opposite sides of the user's scrotum.

2. The device of claim 1 in which said cord member is provided with means for shortening and lengthening said loop so as to place more and less pressure, respectively, at said penis base.

3. The device of claim 1 in which said means for shortening and lengthening said loop comprises a clamp member engageable with and joining opposite ends of said cord member and allowing said ends to be displaced relative to said clamp member for said shortening and lengthening of said loop.

4. The device of claim 1 in which said cord member is hollow, said arc member being encased by a portion thereof.

5. The device of claim 1 in which said arc member is hollow, said cord member passing therethrough.

6. The device of claim 1 in which said arc member is hand deformable allowing said arc member to be slightly deformed to more effectively accommodate the user thereof.

7. The device of claim 1 in which said arc member is provided with a relatively soft cushioning material to provide cushioned contact with said top of said penis.

8. The device of claim 1 including a protuberance projecting outwardly from said arc member to provide clitoral stimulation to the partner of said user during intercourse.

* * * * *